United States Patent [19]

Noble et al.

[11] Patent Number: 4,678,471

[45] Date of Patent: Jul. 7, 1987

[54] METHOD AND APPARATUS FOR PREVENTING ROTATIONAL FAILURE OF ORTHOPEDIC ENDOPROSTHESES

[76] Inventors: Philip C. Noble, 2601 S. Braeswood, #103, Houston, Tex. 77025; Hugh S. Tullos, 2151 Troon Rd., Houston, Tex. 77019; John P. Davidson, 10823 Emery Dr., Houston, Tex. 77099

[21] Appl. No.: 768,284

[22] Filed: Aug. 22, 1985

[51] Int. Cl.⁴ ................................................ A61F 2/28
[52] U.S. Cl. ...................................... 623/16; 623/23; 128/92 VD
[58] Field of Search .................................... 623/16–23; 128/92 XV, 92 XY, 92 R, 92 XK, 92 XW, 92 XJ

[56] References Cited

U.S. PATENT DOCUMENTS

| | | |
|---|---|---|
| 3,782,373 | 1/1974 | Smythe. |
| 4,012,796 | 3/1977 | Weisman et al. |
| 4,284,080 | 8/1981 | Rehder. |
| 4,430,761 | 2/1984 | Niederer et al. |
| 4,441,492 | 4/1984 | Rydell et al. ............... 128/92 XV |
| 4,612,922 | 9/1986 | Barber ............................. 128/92 R |

Primary Examiner—Richard J. Apley
Assistant Examiner—James Prizant
Attorney, Agent, or Firm—Fulbright & Jaworski

[57] ABSTRACT

An apparatus and method for making one or more grooves in the medullary canal surface of a bone to secure and reduce the risk of rotational failure of implanted orthopedic endoprostheses. The apparatus includes a head and, attached thereto, a body adapted for insertion into the medullary canal of a bone. The apparatus also includes a channel therethrough that is enclosed in the head and open in the body. One or more grooves is made in the medullary canal surface of a bone by placing the body of the apparatus in the medullary canal, inserting a cutting device in the channel, and then using the cutting device to remove an amount of bone tissue sufficient to form a groove or grooves. The risk of rotational failure of implanted orthopedic endoprostheses is reduced by implanting prostheses that engage and are secured in place by the groove or grooves.

5 Claims, 5 Drawing Figures

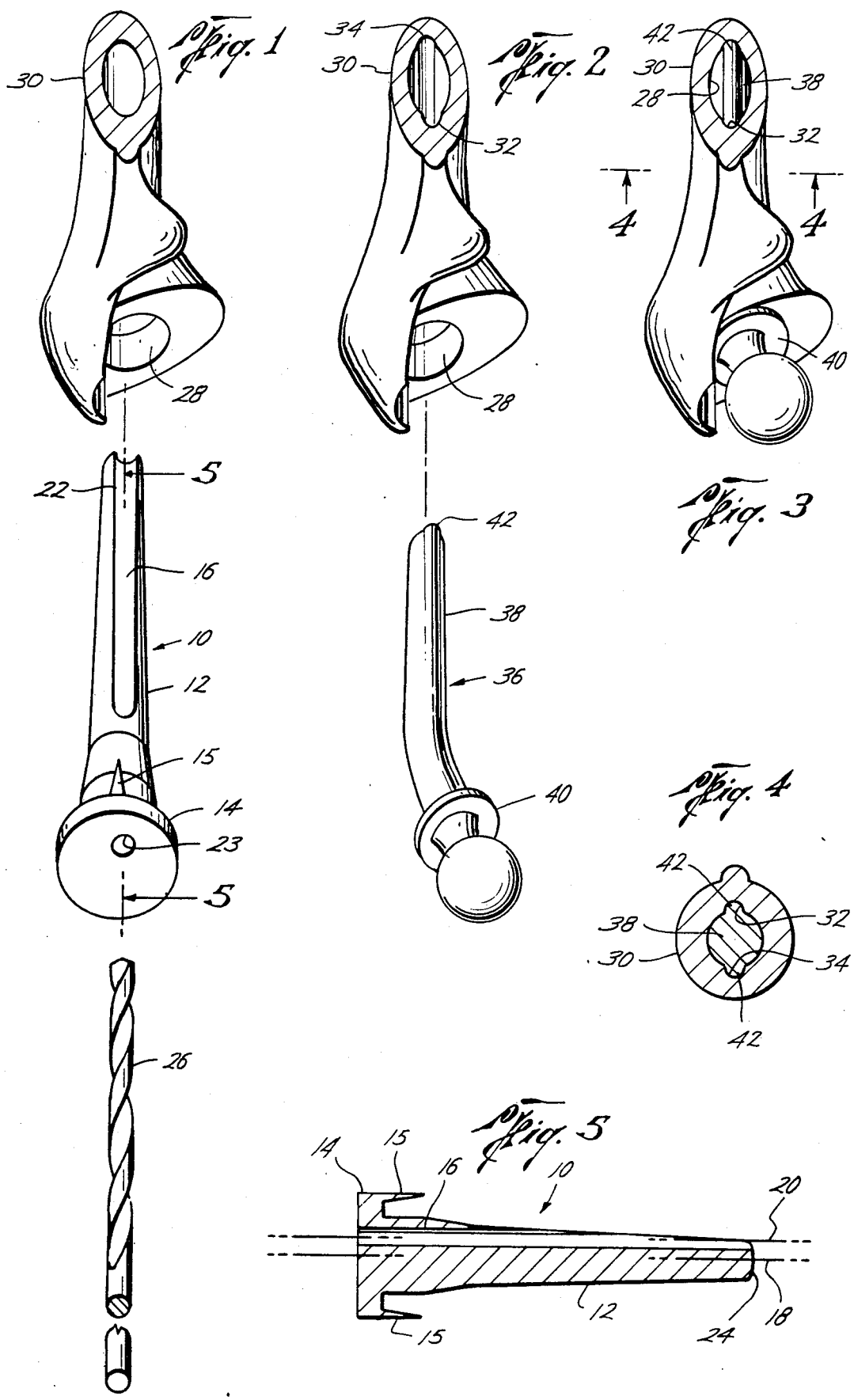

METHOD AND APPARATUS FOR PREVENTING ROTATIONAL FAILURE OF ORTHOPEDIC ENDOPROSTHESES

BACKGROUND OF THE INVENTION

1. Field of the Invention

This invention relates to a method and apparatus for reducing the risk of rotational failure of orthopedic endoprostheses such as femoral prostheses. An apparatus has been designed and a method using this apparatus has been developed to enable making one or more grooves in the medullary canal surface of bones. The risk of rotational failure of the endoprostheses is reduced by implanting endoprostheses that interact with the grooves thereby securing the endoprosthesis in a desired position.

2. Description of Related Art

Each year a great many patients are relieved of severely debilitating injuries by surgical procedures to replace damaged joints. Of the more common of these operations are partial or total hip replacements. Patients suffering from rheumatoid or degenerative arthritis often derive great benefit from these surgical procedures. Additionally, femoral head necrosis requiring replacement with femoral head prostheses can result following fractures of the femur and has been associated with prolonged corticosteroid therapy.

Failure of implanted joint prostheses, however, is a complication often encountered that causes great pain and many times results in having to subject the patient to the risks and trauma of a surgical procedure to replace the failed prostheses. Many endoprostheses fail as a result of excessive loading of interfaces between the endoprosthesis and surrounding bone. As an example, femoral endoprostheses are constructed of a ball portion that extends above the proximal end of the femur and, attached to the ball, a shaft that is inserted into the medullary canal of the femur. Because of the smooth, relatively circular inner surface of the medullary canal of the femur, adequate mechanical stabilization of the endoprosthesis commonly is not attainable within that canal using current surgical methods. Rotation occurs because the materials and methods employed to secure the prosthetic shaft to the femur are unable to withstand the forces exerted upon the hip joint during movement.

To alleviate the pain and risks of further surgery associated with failure of femoral endoprostheses, efforts long have been directed to designing prostheses less likely to rotate and methods for securing these prostheses that produce bonds to the bone that are better able to withstand the torsional forces exerted upon the prostheses. U.S. Pat. No. 4,430,761 discloses a femoral head prosthesis constructed of a shaft provided with numerous parallel grooves which improve mechanical interaction with the cement placed in the bone cavity to bond the shaft to the bone.

U.S. Pat. No. 3,782,373, describes a jig that includes a shaft similar to the shaft of a femoral head prosthesis which jig is used as a guide for drilling holes in the femur to enable proper placement of screws that pass through the bone and engage the shaft of the prosthesis thereby securing it in the desired position.

As disclosed in U.S. Pat. No. 4,012,796, another approach to preventing failure of femoral head prostheses is to place an elastic collar in the proximal end of the femur which collar fits tightly around the prosthetic shaft to secure it in the desired position. Also, this collar is said to reduce the pressure exerted by the shaft of the prostheses on the femur thereby reducing the risk of necrosis which may cause prosthetic failure.

U.S. Pat. No. 4,284,080 discloses a cutting tool for shaping a femoral head to receive a shell-shaped prosthesis. This cutting tool is used to position prostheses that are attached to and supported by the femoral head rather than those that replace completely the previously removed femoral head. This cutting tool includes a blade for forming a cylindrical bore in the center of the femur to position the cutting tool as it shapes the femoral head to receive the prosthesis. To direct the blade that forms the cylindrical bore in the femur, the blade includes a guiding bore that fits over and, as the blade cuts the cylindrical bore, follows a guiding pin previously positioned in the center of the femur.

None of the references cited above and nothing in the prior art known to the present inventors teaches or suggests an apparatus or method for making one or more grooves in the medullary canal surface of a bone to provide surfaces that interact with and thereby reduce the risk of rotational failure of implanted prostheses.

SUMMARY OF THE INVENTION

The present invention is directed to an apparatus and method for making one or more grooves in the medullary canal surface of a bone to secure and reduce the risk of rotational failure of implanted endoprostheses. More particularly, this invention relates to an apparatus adapted for insertion into the medullary canal of a bone, which apparatus includes an element that receives and fixes in a desired position against the surface of the bone forming the medullary canal a cutting device that is used to remove a portion of the bone sufficient to produce a groove in the medullary canal surface of the bone. One presently preferred design of this apparatus includes a solid metal body attached to a head that has a larger cross-sectional area than the body. Beginning in the head, a channel is formed in the apparatus so that the channel is enclosed in the head and open in the body. A presently preferred method of making one or more grooves in the medullary canal surface of a bone includes positioning the apparatus in the medullary canal of a bone, inserting a cutting tool such as a rotary drill bit into the channel in the apparatus, and using the cutting tool to remove a portion of the bone sufficient to form a groove in the medullary canal bone surface.

Accordingly, it is an object of the present invention to provide an apparatus having a round and tapered body adapted for insertion into the medullary canal of a bone, which apparatus includes a channel extending parallel but offset from the axis of the body that receives a cutting tool and positions the cutting tool against the surface of the bone surrounding the medullary canal.

It is a further object of the present invention to provide a method for making one or more grooves in the medullary canal luminal surface of a bone to secure and reduce the risk of rotational failure of implanted endoprostheses.

Other and further objects, features, and advantages will be apparent from the following description of a presently preferred embodiment of the invention, given for the purpose of disclosure and taken in conjunction with the accompanying drawings.

BRIEF DESCRIPTION OF THE DRAWINGS

FIG. 1 is an elevational view of a preferred embodiment of the presently invented apparatus positioned for insertion into the medullary canal of a bone and shows a rotary drill bit for use with the apparatus, FIG. 2 is an elevational view of a bone having grooves in its medullary canal surface formed by use of the presently invented apparatus and shows a femoral head prosthesis positioned for placement in the bone medullary canal, FIG. 3 is an elevational view of a bone with a femoral head prosthesis positioned in the medullary canal of the bone, FIG. 4 is a cross sectional view taken along the lines 4—4 of FIG. 3, looking in the direction of the arrows, and FIG. 5 is a cross sectional view taken along the lines 5—5 of FIG. 1, looking in the direction of the arrows.

DESCRIPTION OF THE PREFERRED EMBODIMENTS

Referring now to FIGS. 1 and 5, an apparatus 10 according to one embodiment of the present invention is shown, which apparatus has a body 12 and head 14 attached to one end of the body 12. Preferably the body 12 is circular and tapered for allowing the body to fit into the natural taper of the medullary canals of bones. The head 14 has a larger cross sectional area than the body 12 so that the body 12 is prevented from slipping entirely into the medullary canal and for rotational adjusting of the body 12 in the medullary canal. The head 14 and body 12 include a channel 16 therein formed generally in the direction of the longitudinal axis 18 of the apparatus 10 but offset from and preferably parallel to the longitudinal axis 18 of the apparatus 10. The channel 16 is positioned in the apparatus 10 so that, in the body 12, the axis 20 of the channel 16 is closer to the external surface of the body 12 than one-half the distance from the axis 20 of the channel 16 to the side 22 of the channel 16. Thus positioned, the channel 16 is enclosed in the head 14 and open on one side in the body 12. Because the taper of the body 12 and the offset of the axis 20 of the channel 16 relative to the axis 18, the axis 20 of the channel 16 becomes closer to the medullary canal bone surface in the direction away from the head 14 to the end 24 of the body 12. Thus, when a drilling means such as a bit 26 is inserted into the channel 16 through port 23 and the medullary canal 28 it will cut a groove of increasing depth in the medullary canal 28.

The apparatus 10 may include rotational positioning means such as spikes 15 which when they engage the bone 30 hold the rotational position of the apparatus 10 relative to the bone 30 while a groove is being cut.

The length and cross sectional area of the body 12 are variable and are selected depending upon the size of the bone 30 in which the apparatus 10 is to be used. The length and cross sectional area of the head also are variable. Additionally, the cross sectional area and shape of the channel 16 are variable to receive cutting tools of different sizes and shapes.

According to the presently preferred method for decreasing the risk of rotational failure of implanted endoprostheses by making one or more grooves in the medullary canal surface of the bone, FIG. 1 shows the apparatus 10 positioned for insertion of the body into the medullary canal 28 of the bone 30. In some cases, the canal 28 is prereamed with a tapered reamer to provide a conical cavity. After the body 12 of the apparatus 10 is inserted into the bone medullary canal 28, a cutting tool 26 is placed in the channel 16. The cutting tool 26 may be a rotary drill bit; however, other cutting tools such as reciprocating saw blades also are functional in this invention. The cutting tool 26 must be of sufficient cross sectional area to extend outside the channel 16 and engage the surface of the bone surrounding the medullary canal 28. The cutting tool 26 placed in the channel 16 then is operated to remove a quantity of the bone surrounding the medullary canal 28 to form a groove in the medullary canal surface of the bone.

Referring now to FIG. 2, a bone 30 is shown having a medullary canal 28. Using the presently preferred apparatus, grooves 32 and 34 have been formed in the surface of the bone surrounding the medullary canal, by making one groove 32, rotating the apparatus 180° and then cutting the second groove 34. A prosthesis 36 consisting of a shaft 38, a head 40, and one or more flanges 42 is shown positioned for insertion of its shaft 38 into the medullary canal 28 of the bone 30. FIG. 3 shows a bone 30 into the medullary canal of which has been placed a prosthesis 36.

FIG. 4 is a cross sectional view of a bone 30 into the medullary canal of which has been placed a shaft 38 of a prosthesis. Into the medullary canal surface of the bone 30, grooves 32 and 34 have been formed using the presently invented apparatus. The flanges 42 on the shaft 38 of the prosthesis engage grooves 32 and 34 thereby reducing the risk of rotational prosthetic failure. In some cases, the prostheses 36 need not require flanges 42 as a suitable surgical adhesive, cement or glue which securely adherest to the prostheses 42 may be inserted into the canal 28 around the prostheses and fills the grooves 32 and 34 and prevents rotation of the prostheses 36. Although in this example two grooves were formed in the medullary canal surface of the bone, it can be seen that the risk of rotational failure of implanted prostheses is reduced by forming one or more grooves in the medullary canal surface of the bone.

The present invention, therefore, is well adapted to carry out the objects and attain the ends and advantages mentioned as well as others inherent therein. While a presently preferred embodiment of the invention is given for the purpose of disclosure, numerous changes in the details of construction and arrangement of parts and steps of the method may be made which readily will suggest themselves to those skilled in the art and which are encompassed within the spirit of the invention and the scope of the appended claims.

What is claimed is:

1. A method for reducing the risk of rotational failure of a prosthesis positioned in the medullary canal of a bone, comprising:
    making a groove in the medullary canal surface of a bone; and
    inserting into the medullary canal a prosthesis securable in a desired position using the groove in the medullary canal bone surface thereby reducing the risk of rotational prosthetic failure.

2. The method of claim 1, wherein making a groove in the medullary canal surface of the bone, comprises:
    inserting into the medullary canal of a bone an apparatus comprised of a body for insertion into the medullary canal of a bone and, attached to the body, means for positioning cutting means against the medullary canal surface of the bone;

placing the cutting means into the means for positioning cutting means; and using the cutting means to remove an amount of bone sufficient to make a groove in the medullary canal surface of the bone.

3. The method of claim 1, wherein making one or more grooves in the medullary canal surface of the bone, comprises:

inserting into the medullary canal of a bone an apparatus comprised of a head attached to a body, the cross-sectional area of the head being greater than the cross-sectional area of the body, the head and body having a channel therein extending generally longitudinally of the axis of the body, the axis of the channel being closer to the external surface of the body than one-half the width of the channel so that the channel is open in the body and closed in the head;

placing cutting means into the channel so that the cutting means extends into the channel in the body and engages the medullary canal surface of the bone; and using the cutting means placed in the channel to remove an amount of bone from the medullary canal surface of the bone to form a groove in the medullary canal bone surface.

4. The method of claim 1, wherein the cutting means is a rotary drill bit.

5. A method for making a groove in the medullary canal surface of a bone for receiving a prosthesis having a longitudinally extending flange, comprising:

inserting into the medullary canal of a bone a tapered body having a longitudinally extending channel extending out of the outer periphery of a portion of the body; and inserting a cutting tool into the channel and drilling a longitudinally extending groove in the medullary canal surface of the bone.

* * * * *